United States Patent
Simms

(10) Patent No.: US 6,284,719 B1
(45) Date of Patent: Sep. 4, 2001

(54) TWO PACK SYSTEM FOR THE PREPARATION OF PERACID COMPOSITIONS FOR TEAT-DIPS

(76) Inventor: Robert Ashley Simms, 3 Walnut Close, Woolston, Warrington, Cheshire WA1 4HA (GB)

( * ) Notice: Subject to any disclaimer, the term of this patent is extended or adjusted under 35 U.S.C. 154(b) by 0 days.

(21) Appl. No.: 09/532,425

(22) Filed: Mar. 23, 2000

Related U.S. Application Data

(63) Continuation of application No. PCT/GB98/02708, filed on Sep. 9, 1998.

(30) Foreign Application Priority Data

Sep. 25, 1997 (GB) .................................................. 9720287

(51) Int. Cl.⁷ ............................ C11D 3/48; C11D 12/00; A01N 39/00
(52) U.S. Cl. .......................... 510/160; 510/383; 510/419; 424/616
(58) Field of Search .................................. 510/160, 383, 510/419; 424/616

(56) References Cited

U.S. PATENT DOCUMENTS

| | | | | |
|---|---|---|---|---|
| 5,279,735 | * | 1/1994 | Cosentino | 210/321.69 |
| 5,451,346 | * | 9/1995 | Amou et al. | 252/186.23 |
| 5,616,335 | * | 4/1997 | Nicolle et al. | 424/405 |
| 5,720,983 | * | 2/1998 | Malone | 424/616 |
| 5,733,474 | * | 3/1998 | Kagermeirer et al. | 252/186.25 |
| 5,962,392 | * | 10/1999 | Revell et al. | 510/372 |

FOREIGN PATENT DOCUMENTS

| | | | |
|---|---|---|---|
| 0 596 493 | 5/1994 | (EP) | A01N/37/16 |
| 0 658 309 | 6/1995 | (EP) | A01N/59/00 |
| WO 94/15465 | 7/1994 | (WO) | A01N/37/16 |
| WO 94/24863 | 11/1994 | (WO) | A01N/37/16 |

OTHER PUBLICATIONS

*Chemical Abstracts, vol. 104*, p. 192 (1986).
*Chemical Abstracts, vol. 104*, p. 339 (1986).

* cited by examiner

*Primary Examiner*—Yogendra N. Gupta
*Assistant Examiner*—John M Petruncio
(74) *Attorney, Agent, or Firm*—Marshall, O'Toole, Gerstein, Murray & Borun

(57) ABSTRACT

A two-pack system for the preparation of peracid compositions for the disinfection, cleaning, and protection of cow's teats before and after milking. A first component of the product comprises an aqueous equilibrated solution of a lower aliphatic peracid and a second component comprises an aqueous solution containing an emollient, food grade fragrance, food grade dye, food grade thickening agent, and alkali buffer. The two packs can be mixed to produce a consistent solution of known quality for reducing disease on cow's teats that is nonirritant, has low odor and/or contains a food grade fragrance and may be colored, thickened, pH buffered, and is effective for at least 24 hours after mixing.

35 Claims, No Drawings

TWO PACK SYSTEM FOR THE PREPARATION OF PERACID COMPOSITIONS FOR TEAT-DIPS

CROSS-REFERENCE TO RELATED APPLICATIONS

This application is a continuation of international application Ser. No. PCT/GB98/02708, filed Sep. 9, 1998, the entire disclosure of which is incorporated by reference.

DESCRIPTION

A two pack system for the preparation of peracid compositions for teat-dips. The present invention relates to the disinfection of cow's teats before and after milking to reduce bacteria and protect the skin. It relates in particular to improvements and additions to a prior Patent Application (Number 9720287.3; Filing Date Sep. 25, 1997)

Dairy farmers mill cows two or in some cases three times per day. Although pre-milking disinfectants are now becoming more readily available the general practice is to spray or dip the teat after milking to reduce bacteria, reduce the risk of disease and problems with individual cows to ensure the best quality of milk.

The teat-dip products available are largely based on chlorhexidine or iodine as the active disinfecting ingredient and generally contain emollients (moisturizers) to preserve the quality of the skin and prevent cracking or irritation Peracetic acid has been used in the past with dilution from basic equilibrated formulations but can cause problems due to initancy through too high concentrations, acidic pH and/or the absence of moisturizers to preserve skin quality.

Peracetic acid can be formulated with emolients as is the case with a concentrated product, Upersan, available from Kesla Chemie GMBH in Germany, which requires a dilution of 1 part in 9 parts water prior to use and is claimed to be stable for 24 hours at ambient or 48 hours at 8° C. The product on dilution has an active peracetic acid level of approximately 1100 ppm which is effective against bacteria, particularly mastitis and is non-irritant.

The Kesla product has a number of limitations which the present invention overcomes. The first is that it is diluted with water of unknown quality which restricts its in-use life due to degradation and decomposition of the final diluted product. Although it has an acidic pH it is lower than the pH of cow's skin and increases the risk (if the dilution is not accurate) of irritancy due to pH. It has an unpleasant odor even after dilution and contains no color which is of use to the farmer to indicate which teats have been treated. It also has no noticeable thickness or viscosity.

According to the present invention all these limitations are overcome by using two separate packs made up of an equilibrated solution of peracetic acid and a second solution used to dilute the peracetic acid at the time of use.

The second (diluent) solution is consistant in make-up and of known quality improving the claimed use life of the product. Patent Application (Number 9720287.3) refers to the inclusion of sodium hydroxide as an alkali buffer but it may be substituted with alternative alkali buffers such as bi-carbonates or other metal hydroxides. Furthermore the correct choice of peracetic acid may allow a lower quantity of alkali buffer to be included or omitted altogether whilst the two pack system allows recognized thickeners such as vegetable gums to be incorporated to further enhance the physical properties of the final in-use product.

An example of the second diluent solution is that it contains a food grade fragrance in combination with emolients (skin moisturizers) and/or thickeners which would normally be expected to decompose the peracetic acid or be degraded due to reaction with the peracetic acid. It can also contain a dye that assists in identifying which teats have been treated but again would be expected to react directly with the peracetic acid and disappear (bleach) if supplied in a single pack.

Correct choice and concentration of the fragrance and/or dye can also indicate the useful life of the final mixed solution through fading or disappearance after a set period prompting disposal and replacement with fresh product.

The invention also focuses on the best choice of equilibrated peracetic acid solution with recommendation that it should contain the lowest possible ratio of peracetic acid to acetic acid to give a final in-use solution with a pH closer to that of the cow's skin and lower odor due to much lower levels of acetic acid.

The addition of an alkali buffer such as metal hydroxide, carbonate or bi-carbonate can also be incorporated into the second (diluent) solution to improve the pH but is not essential if the correct initial peracetic a grade is chosen.

Based on current knowledge the combination of all these components in a single solution would result in an unstable product and therefore it is essential to separate the highly oxidizing and potentially unstable peroxygen solution from the other components until the of use.

Dairy farmers can purchase the two separate packs safe in the knowledge that they can be stored for acceptable periods without degradation and only become active when combined. The final formulation can be prepared to ensure a visible indication (color change eg. blue to clear) to the farmer that the solution is no longer viable and should be replaced.

This invention concerns a two pack system for preparing teat-dip compositions and uses of such compositions.

More particular the present invention concerns compositions comprising dilute aqueous solutions of lower aliphatic peracids and their use as teat-dip compositions. This invention relates specifically to combining solutions of peracetic acid with components that are likely to cause destabilisation or incompatibility over prolonged periods (greater than seven days). The two pack system allows the compositions that are considered destabilizing or incompatible to be segregated prior to mixing at the time of use. In addition to segregating the various components on the grounds that the overall shelf-life expectancy of the respective products will be extended it also takes into account the best ratio of components in the peracetic acid (peracetic acid, acetic acid, hydrogen peroxide and water) to provide a final solution that is effective for at least 24 hours after mixing and preferably one week, non-initant, has low odor and/or contains a food acceptable fragrance, may be colored, thickened and pH buffered.

I claim:

1. A two-pack system for the preparation of a disinfectant dye treatment-indicated teat-dip composition comprising a first pack containing a first aqueous equilibrated solution comprising a ($C_2$–$C_9$) aliphatic peracid, a ($C_2$–$C_9$) aliphatic acid, and hydrogen peroxide, and a second pack containing a second aqueous diluent solution comprising a dye which allows for dilution of said first aqueous equilibrated aliphatic peracid-containing solution.

2. The two-pack system according to claim 1 wherein the dye of the second aqueous solution is bleachable by conditions in the first aqueous solution.

3. The two-pack system according to claim 1 wherein the second aqueous solution comprises the dye in an amount from 0.0001% to 0.5% by weight.

4. The two-pack system according to claim 1 wherein the second aqueous solution comprises the dye in an amount from 0.0001% to 0.1% by weight.

5. The two-pack system according to claim 1 wherein the second aqueous solution comprises an emollient in an amount from 5.0% to 50.0% by weight.

6. The two-pack system according to claim 1 wherein the second aqueous solution comprises an emollient in an amount from 5.0% to 20.0% by weight.

7. The two-pack system according to claim 5 wherein the emollient of the second aqueous solution is 1,2,3-propane triol.

8. The two-pack system according to claim 5 wherein the emollient of the second aqueous solution is 1,2,3,4,5,6-hexanehexol.

9. The two-pack system according to claim 5 wherein the emollient of the second aqueous solution is glycerol diacetate.

10. The two-pack system according to claim 1 wherein the second aqueous solution comprises a thickening agent in an amount from 0.01% to 50% by weight.

11. The two-pack system according to claim 1 wherein the second aqueous solution comprises a thickening agent in an amount from 0.01% to 20% by weight.

12. The two-pack system according to claim 1 wherein the second aqueous solution comprises a thickening agent in an amount from 0.01% to 10% by weight.

13. The two-pack system according to claim 1 wherein the second aqueous solution further comprises an alkali buffering agent in an amount from 0.001% to 5% by weight.

14. The two-pack system according to claim 1 wherein the second aqueous solution further comprises a fragrance in an amount from 0.0001% to 0.5% by weight.

15. The two-pack system according to claim 1 wherein the second aqueous solution comprises a fragrance in an amount from 0.01% to 0.5% by weight.

16. The two-pack system according to claim 1 wherein the first aqueous solution comprises the ($C_2$–$C_9$) aliphatic peracid in an amount from 0.1% to 7% by weight.

17. The two-pack system according to claim 1 wherein the first aqueous solution comprises the ($C_2$–$C_9$) aliphatic peracid in an amount from 0.1% to 5% by weight.

18. The two-pack system according to claim 1 wherein the ($C_2$–$C_9$) aliphatic peracid of the first aqueous solution is peracetic acid, and the ($C_2$–$C_9$) aliphatic acid of the first aqueous solution is acetic acid.

19. The two-pack system according to claim 18 wherein the first aqueous solution comprises peracetic acid and acetic acid in a percentage by weight ratio of between 1:1 and 1:15.

20. The two-pack system according to claim 18 wherein the first aqueous solution comprises peracetic acid and acetic acid in a percentage by weight ratio of between 1:1 and 1:3.

21. The two-pack system according to claim 18 wherein the first aqueous solution comprises peracetic acid and acetic acid in a percentage by weight ratio of between 1:1 and 1:2.

22. The two-pack system according to claim 18 wherein the first aqueous solution comprises peracetic acid and hydrogen peroxide in a percentage by weight ratio of between 1:3 and 1:12.

23. The two-pack system according to claim 18 wherein the first aqueous solution comprises peracetic acid and hydrogen peroxide in a percentage by weight ratio of between 1:6 and 1:12.

24. The two-pack system according to claim 18 wherein the first aqueous solution comprises peracetic acid and hydrogen peroxide in a percentage by weight ratio of between 1:10 and 1:12.

25. The two-pack system according to claim 1 wherein the first aqueous solution is an equilibrated solution.

26. A process for the preparation of a disinfectant dye treatment-indicated teat-dip composition comprising mixing a first pack containing a first aqueous equilibrated solution comprising a ($C_2$–$C_9$) aliphatic peracid, a ($C_2$–$C_9$) aliphatic acid, and hydrogen peroxide, with a second pack containing a second aqueous diluent solution comprising a dye which effect dilution of said first aqueous equilibrated aliphatic peracid-containing solution.

27. A process according to claim 26 wherein the first pack and the second pack are mixed in a ratio of between 1:5 and 1:60.

28. A process according to claim 26 wherein the first pack and the second pack are mixed in a ratio of between 1:9 and 1:45.

29. A process according to claim 26 wherein the first pack and the second pack are mixed in a ratio of between 1:25 and 1:35.

30. A disinfectant dye treatment-indicated teat-dip composition obtainable by a process comprising mixing a first pack containing a first aqueous equilibrated solution comprising a ($C_2$–$C_9$) aliphatic peracid, a ($C_2$–$C_9$) aliphatic acid, and hydrogen peroxide, with a second pack containing a second aqueous diluent solution comprising a dye thereby effecting dilution of said first aqueous equilibrated aliphatic peracid-containing solution.

31. The disinfectant composition according to claim 30 wherein the first pack and the second pack are mixed in a ratio of between 1:5 and 1:60.

32. The disinfectant composition according to claim 30 wherein the first pack and the second pack are mixed in a ratio of between 1:9 and 1:45.

33. The disinfectant composition according to claim 30 wherein the first pack and the second pack are mixed in a ratio of between 1:25 and 1:35.

34. The disinfectant composition according to claim 30, wherein the composition comprises an initial concentration of peracetic acid of between 0.01% and 0.2% by weight.

35. The disinfectant composition according to claim 30, wherein the composition comprises an initial concentration of peracetic acid of between 0.03% and 0.12% by weight.

* * * * *